US00PP19139P2

(12) United States Plant Patent
Smit

(10) Patent No.: US PP19,139 P2
(45) Date of Patent: Aug. 26, 2008

(54) ***IMPATIENS* PLANT NAMED 'SILTE ROR07'**

(50) Latin Name: *Impatiens walleriana*
Varietal Denomination: Silte Ror07

(75) Inventor: Erik Smit, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/807,395

(22) Filed: May 29, 2007

(51) Int. Cl.
*A01H 5/00* (2006.01)

(52) U.S. Cl. ..... Plt./317
(58) Field of Classification Search ..... Plt./317
See application file for complete search history.

*Primary Examiner*—Kent L. Bell
(74) *Attorney, Agent, or Firm*—Jondle & Associates, P.C.

(57) ABSTRACT

A new *Impatiens* plant particularly distinguished by double, rose-shaped, rose flowers, semi-compact, upright, outwardly spreading and mounded plant habit, free flowering, good basal branching, and moderately vigorous growth habit, is described.

1 Drawing Sheet

Genus and species: *Impatiens walleriana.*
Variety denomination: 'Silte Ror07'.

BACKGROUND OF THE NEW PLANT

The present invention comprises a new and distinct cultivar of *Impatiens,* botanically known as *Impatiens walleriana* and hereinafter referred to by the cultivar name 'Silte Ror07'. The new cultivar originated from a sib cross made in June 2004 in Andijk, The Netherlands. The parents were the proprietary red star-flowered *Impatiens* plant 'ID03-20-5' (unpatented) and the proprietary red star-flowered *Impatiens* plant 'ID03-20-7' (unpatented). The seeds produced by the sib cross were sown in September 2004. A single plant selection was chosen for further evaluation and for asexual propagation in December 2004.

The new cultivar was created in 2004 and has been asexually reproduced repeatedly by vegetative cuttings and tissue culture in Andijk, The Netherlands and Gilroy, Calif. over a two-year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar were applied for with the European Union on Dec. 14, 2006, in Canada on Apr. 19, 2006 and in Japan on Nov. 1, 2006.

SUMMARY OF THE INVENTION

The following are the most outstanding and distinguishing characteristics of this new cultivar when grown under normal horticultural practices in Gilroy, Calif. and Andijk, The Netherlands.

1. Double, rose-shaped, rose flowers;
2. Semi-compact, upright, outwardly spreading and mounded plant habit; and
3. Free flowering, good basal branching and moderately vigorous growth habit.

DESCRIPTION OF PHOTOGRAPH

This new *Impatiens* plant is illustrated by the accompanying photograph which shows the overall plant habit including blooms, buds, and foliage of the plant; the colors shown are as true as can be reasonably obtained by conventional photographic procedures. The photograph is of a whole plant about 15 to 16 weeks old, grown in a greenhouse in Hillscheid, Germany during the spring. The photograph was taken in September 2006.

DESCRIPTION OF THE NEW CULTIVAR

Figure 1:
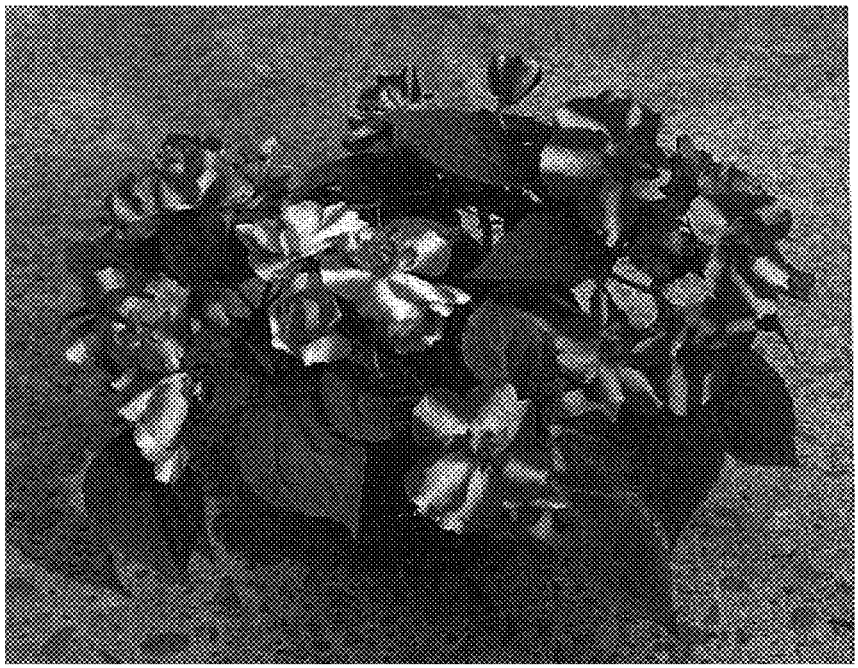
FIG. 1 shows the overall plant habit including blooms, buds, and foliage.
Figure 2:
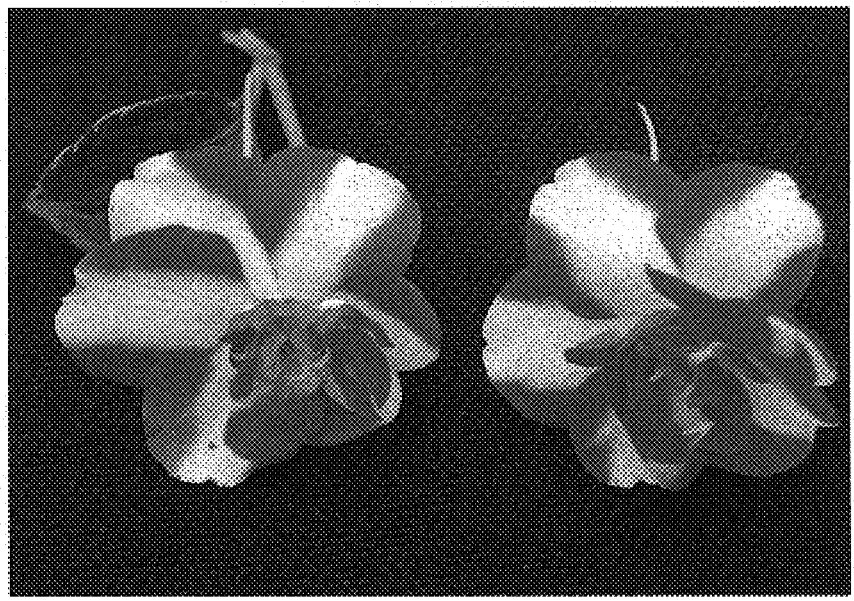
FIG. 2 shows a close-up of the mature flower.

The following detailed descriptions set forth the distinctive characteristics of 'Silte Ror07'. The data which defines these characteristics were collected from asexual reproductions carried out in Gilroy, Calif. in a trial setting. The plant history was taken on 26-week-old plants grown in 6-inch containers in a greenhouse during the fall and winter seasons. The plants had one plant growth regulator treatment and one terminal pinch after cuttings were transplanted. Color readings were taken under-natural light in the greenhouse in January. Color references are primarily to the R.H.S. Colour Chart of The Royal Horticultural Society of London (R.H.S.) (2001). Texture description data was viewed with a dissecting microscope.

DETAILED BOTANICAL DESCRIPTION OF THE NEW PLANT

Classification:
*Family.*—Balsaminaceae.
*Botanical.—Impatiens walleriana.*
*Common name.*—Impatiens.

Parentage:
*Female.*—'ID03-20-5' a proprietary red star-flowered *Impatiens* plant (unpatented).
*Male.*—'ID03-20-7' a proprietary red star-flowering *Impatiens* plant (unpatented).

Growth:

*Form.*—Semi-compact, upright, outwardly spreading and mounded plant habit.

*Growth and branching habit.*—Free flowering, good basal branching, moderately vigorous, pinching of the terminal apices enhances branching.

*Height (from soil level to top of blooms).*—20.0 cm to 25.0 cm.

*Width (including flowers).*—41.0 cm to 46.0 cm.

*Time to produce a finished flowering plant.*—About 8 to 10 weeks for a 4-inch pot.

*Outdoor plant performance.*—Use in shade to semi-shade, use in hanging baskets, mixed containers, window boxes and mass plantings.

*Time to initiate and develop roots.*—Approximately 16 to 21 days at 22° C.

*Root description.*—Fibrous, fleshy, white.

Branches:

*Stem.*—Color: RHS 138B with anthocyanin blotches of RHS 176B. Length: 25.0 cm to 30.0 cm. Diameter: 0.5 cm to 0.6 cm. Internode length: 0.5 cm to 1.5 cm. Texture: Glabrous.

*Peduncle.*—Color: RHS 145A. Length: 3.0 cm to 3.5 cm. Diameter: 0.15 cm to 0.2 cm. Texture: Glabrous.

Leaves:

*Arrangement.*—Mostly alternate in whorls.

*Size.*—Length: 5.3 cm to 5.7 cm. Width: 2.8 cm to 3.3 cm.

*Shape.*—Ovate to broadly ellitptical.

*Apex.*—Cuspidate.

*Base.*—Attenuate.

*Margin.*—Crenate, with ciliation.

*Color (immature leaves).*—Upper surface: Closest to RHS 137A. Lower surface: Closest to RHS 138A with blotches of anthocyanin a little darker than RHS 176B.

*Color (mature leaves).*—Upper surface: A little darker than RHS 137A. Lower surface: RHS 138B with blotches of anthocyanin a little lighter than RHS 176C.

*Texture.*—Glabrous.

*Venation color.*—RHS 138B.

*Petioles.*—Length: 1.5 cm to 2.0 cm. Diameter: 0.3 cm. Color: RHS 138B. Texture: Glabrous.

Flower buds:

*Shape.*—Ovate.

*Size.*—Length: 1.1 cm to 1.3 cm. Diameter: 1.0 cm to 1.2 cm.

*Color at tight bud.*—RHS 52A.

Inflorescence:

*Blooming habit.*—Continuous and freely, all through the year, depending on light levels.

*Type.*—Raceme in leaf axis.

*Number of flowers per inflorescence.*—4 to 6.

*Lastingness of the individual blooms.*—About 5 to 7 days depending on environmental conditions.

*Fragrance.*—None.

Flowers:

*Form and shape of corolla.*—Double-type, rose-shaped bud opening to form a full round flower.

*Corolla size.*—Width: 3.7 cm to 4.0 cm. Depth: 1.5 cm to 1.6 cm.

*Number of petals per flowers.*—12 to 20.

Petals:

*Shape.*—Broadly obovate.

*Apex.*—Emarginate.

*Base.*—Attenuate.

*Margin.*—Entire.

*Petal size.*—Length: 1.9 cm to 2.4 cm. Width: 1.9 cm to 2.0 cm.

*Color.*—Immature petals: Upper surface: RHS N57A. Lower surface: RHS 52B. Mature petals: Upper surface: RHS N57A, fading at maturity to RSH N66A. Lower surface: RHS 54B.

*Texture.*—Glabrous.

Sepals:

*Quantity.*—5; 2 large sepals, 1 modified sepal with a spur and 2 small sepals.

*Texture.*—Glabrous.

*Large sepals.*—Color: RHS N155B; RHS 144A keel. Length: 1.0 cm to 1.1 cm. Width: 0.7 cm to 1.0 cm. Shape: Broadly elliptical. Apex: Cuspidate. Base: Fused. Margin: Entire. Spur: Color: RHS 145A. Length: 2.6 cm to 2.8 cm. Diameter: 0.1 cm.

*Small sepals.*—Color: RHS 144A; RHS 146C apex. Length: 0.2 cm. Width: 0.1 cm. Shape: Ovate. Apex: Acute. Margin: Entire. Base: Fused.

Reproductive organs: Usually not developed and observed.

Fruit and Seed Set: No seed set observed.

Disease and insect resistance: No particular resistance or susceptibility has been observed.

COMPARISON WITH PARENTAL AND COMMERCIAL CULTIVARS

'Silte Ror07' differs from the female parent 'ID03-20-5' in that 'Silte Ror07' has a double rose flower, while 'ID03-20-5' has a single red flower. Additionally, 'Silte ROR07' is more compact with better vigor than 'ID03-20-5'.

'Silte Ror07' differs from the male parent 'ID03-20-7' in that 'Silte Ror07' has a double, rose flower, while 'ID03-20-7' has a single, red flower. Additionally, 'Silte ROR07' is more compact with smaller leaves than 'ID03-20-7'.

'Silte Ror07' differs from the commercial cultivar 'Sparkler Rose' (U.S. Plant Pat. No. 9,603) in that 'Silte ROR07' has narrower leaves with more brownish-red anthocyanins than 'Sparkler Rose'. 'Silte Ror07' has a greener stem with more brownish-red anthocyanins and a shorter spur than 'Sparkler Rose'. Additionally, 'Silte Ror07' has a flower color with more white down the middle of the petal, while 'Sparkler Rose' has a flower color with white only at the apex of the petal.

I claim:

1. A new and distinct cultivar of *Impatiens* plant as shown and described herein.

* * * * *